United States Patent [19]

Rosenbluth et al.

[11] Patent Number: 5,312,423
[45] Date of Patent: May 17, 1994

[54] APPARATUS AND METHOD FOR LAPARAOSCOPIC LIGATION

[75] Inventors: Robert F. Rosenbluth, Laguna Niguel; Rodney A. Brenneman, Mission Viejo, both of Calif.

[73] Assignee: Advanced Surgical Intervention, Inc., San Clemente, Calif.

[21] Appl. No.: 955,353

[22] Filed: Oct. 1, 1992

[51] Int. Cl.$^5$ .......................................... A61B 17/00
[52] U.S. Cl. ................................... 606/148; 606/139
[58] Field of Search ............... 606/139, 144, 145, 148, 606/150, 151, 158, 205–206, 208

[56] References Cited

U.S. PATENT DOCUMENTS

| | | | |
|---|---|---|---|
| 86,016 | 1/1869 | Howell | 606/206 |
| 1,400,653 | 12/1921 | Barbour. | |
| 1,545,682 | 7/1925 | Nelson. | |
| 2,455,833 | 12/1948 | Trombetta. | |
| 2,579,192 | 12/1951 | Kohl. | |
| 3,040,747 | 6/1962 | Wood. | |
| 3,985,138 | 10/1976 | Jarvik. | |
| 5,026,379 | 6/1991 | Yoon | 606/151 |
| 5,037,433 | 8/1991 | Wilk et al. | 606/144 |
| 5,059,201 | 10/1991 | Asnis. | |
| 5,144,961 | 9/1992 | Chen et al. | 606/148 |

FOREIGN PATENT DOCUMENTS

| | | | |
|---|---|---|---|
| 163445 | 7/1949 | Austria. | |
| 2713386 | 11/1978 | Fed. Rep. of Germany | 606/205 |
| 0117617 | 2/1958 | U.S.S.R. | 606/205 |
| 549146 | 3/1977 | U.S.S.R.. | |
| 479719 | 3/1938 | United Kingdom. | |

OTHER PUBLICATIONS

*Endoscopic Sutiring and Knot Tying Manual,* ETHI-CON, a Johnson and Johnson Company, pp. 1–20, published 1991.

*Primary Examiner*—Stephen C. Pellegrino
*Assistant Examiner*—Jeffrey A. Schmidt
*Attorney, Agent, or Firm*—Klein & Szekeres

[57] ABSTRACT

A laparoscopic ligation device comprises an elongate hollow tube, having an open distal end. An arcuate finger, attached to the tube, has a tip that is distally spaced from the distal end of the tube. The finger includes structure adjacent its tip that releasably holds the tag end of a length of suture. A hollow mandrel is disposed within the tube, for movement between extended and withdrawn positions. The mandrel has an open distal end, carrying a plurality of loops formed in the standing part of the suture, that extends distally from the open end of the tube in the extended position. A rod having a hook at its distal end is disposed within the mandrel for movement between extended and withdrawn positions. In use, the finger is manipulated to engage a vessel or duct. The rod is moved to its extended position so that its hook snags the suture tag end from the finger tip. The rod is then moved toward its withdrawn position, carrying the tag end to form a ligature loop around the vessel or duct, and then into the distal end of the mandrel, and through the loops thereon. The mandrel is moved to its withdrawn position, thereby dropping the loops onto the tag end to form a loose knot that is tightened by the continued movement of the rod to its withdrawn position to constrict the ligature loop around the duct or vessel. The knot is then cut away from the rest of the suture.

41 Claims, 8 Drawing Sheets

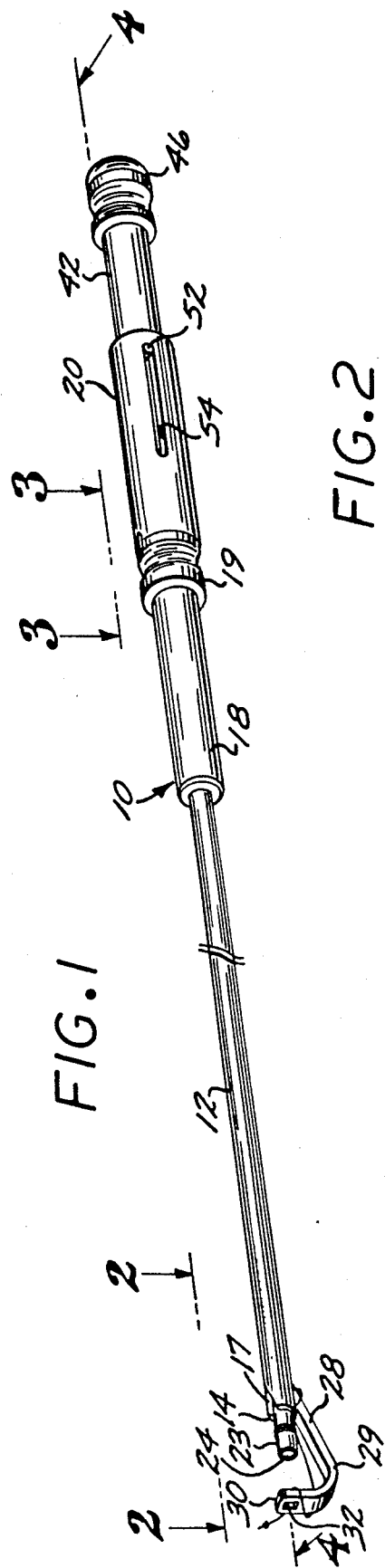
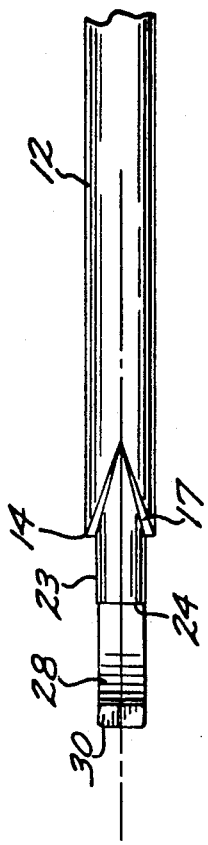
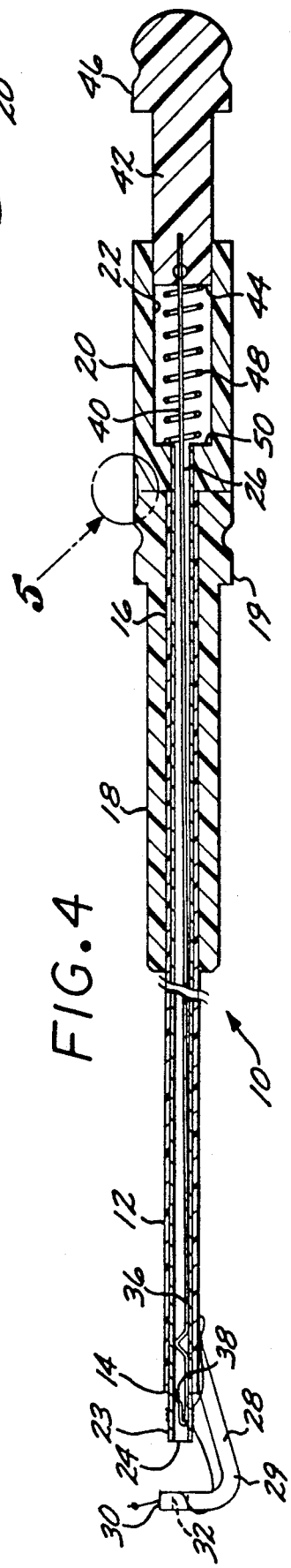
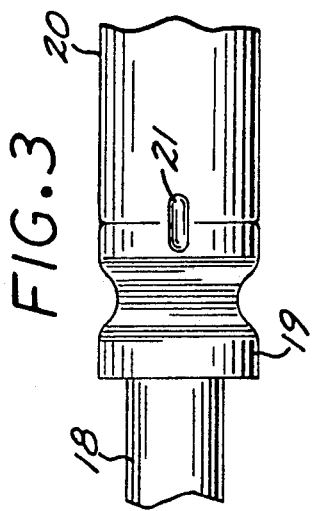

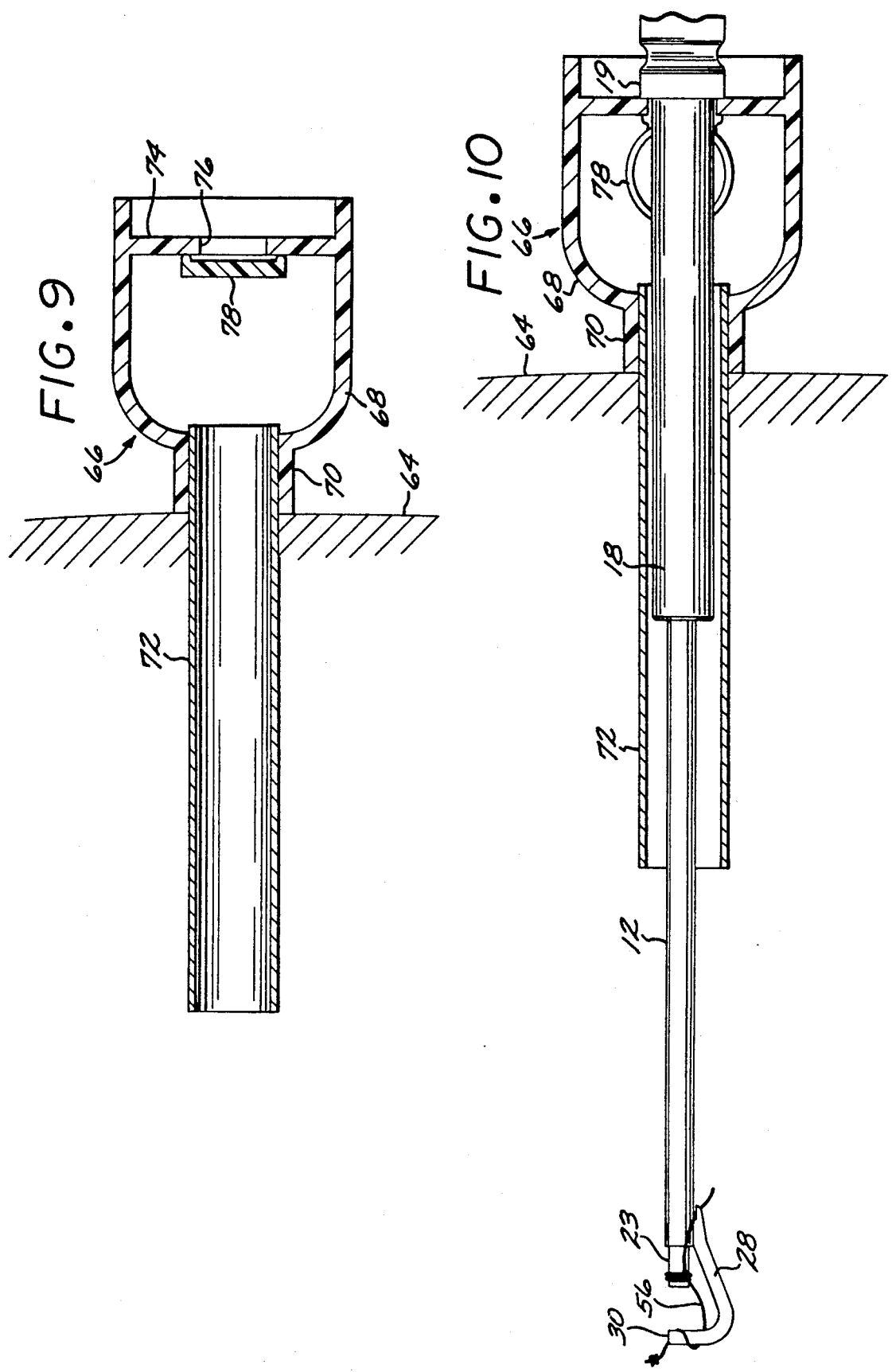

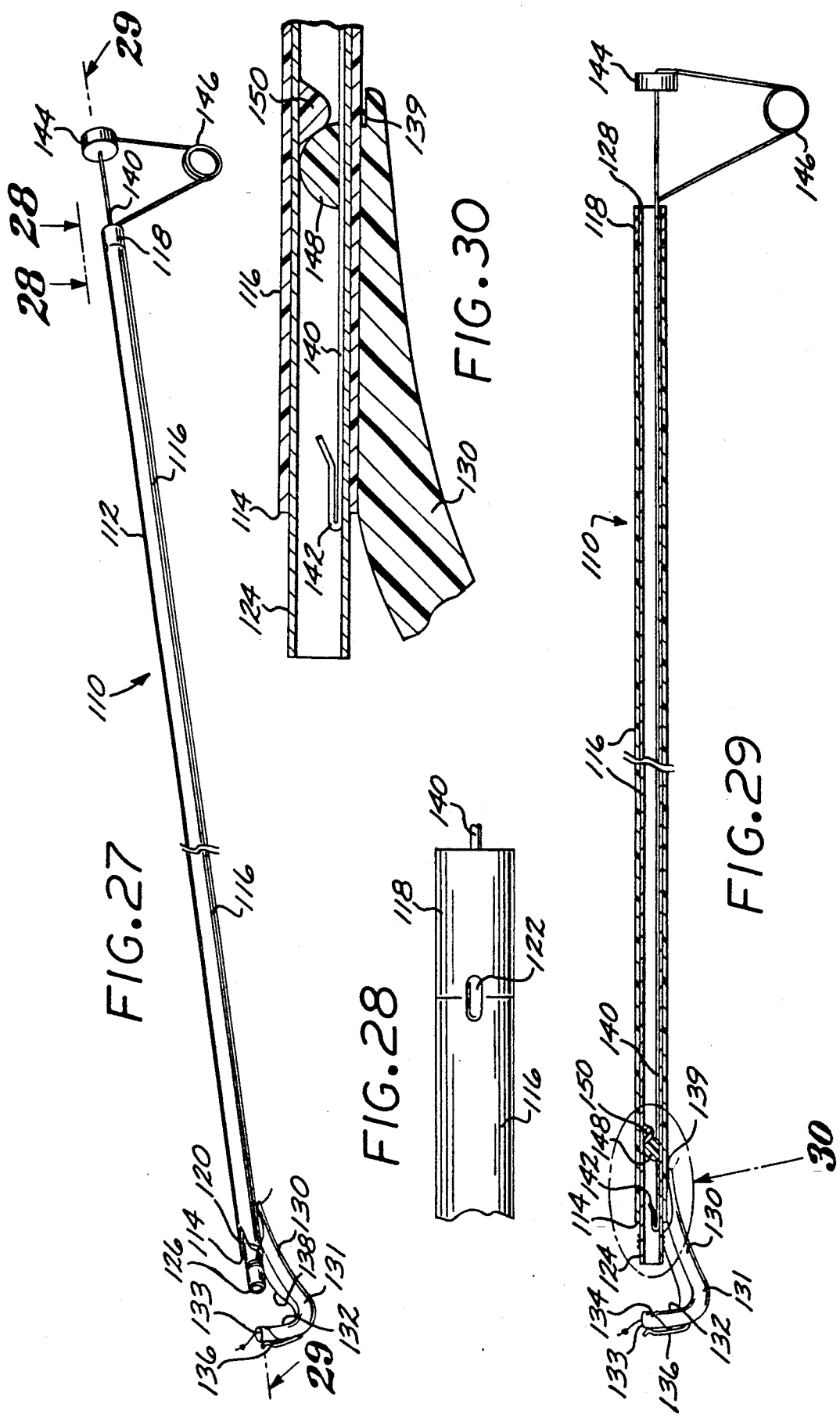

APPARATUS AND METHOD FOR LAPARAOSCOPIC LIGATION

BACKGROUND OF THE INVENTION

This invention relates generally to the field of surgical instruments and methods. More particularly, it relates to an apparatus and method for suture ligation of blood vessels and other bodily ducts, using a laparoscopic access site.

Laparoscopy has become increasingly popular as a technique of minimally invasive surgery because of its significant advantages over conventional surgical techniques: reduced surgical trauma and scarring, substantially less pain and discomfort, significantly decreased risks of infection, and shortened recuperation times (and thus shorter, less expensive hospital stays). Thus, laparoscopy has been used in such procedures as cholecystectomy, hysterectomy, bowel resection, and hernia repair.

In laparoscopy, all of the steps of a surgical procedure (such as dissection, cutting, suturing, and ligating) are performed by means of elongated instruments that are inserted into the abdominal cavity via trocars that, in turn, are inserted through small, "minimally invasive" incisions or punctures.

One of the more difficult surgical skills to acquire is that of laparoscopic knot-tying or ligation of vessels and tissue pedicles and the like. Ligation of such structures during laparoscopy requires the passing of sutures and the tying of knots remotely, using elongated forceps, under videoscopic observation. Several devices have come into use to facilitate laparoscopic ligation, but these have either required the use of clips that may be prone to dislodgement, or the use of preformed suture loops that necessitate the cutting of the vessel prior to tightening the knot, so that the loop may be placed around a free end of the vessel, (which may be disadvantageous in some procedures). Furthermore, some prior art devices may require the surgeon to learn complicated new knots, or they may require additional access sites to complete or tighten the knot.

While there have been a number of suture-tying or ligation devices developed in the prior art, none of these is particularly well-suited to laparoscopic procedures.

For example, Soviet Union Patent No. 549,146 discloses a device for applying ligatures to a blood vessel or the like, comprising an elongate, hollow body having a conical head, and a hook extending from the body so that its terminus is spaced from and opposed to the head. The hook has a grooved aperture near its terminus. A length of ligature is wrapped around the body near the head in one or more loops, and includes a segment that is carried in the groove across the aperture. A retractable rod is carried in the body, the rod having a finger at one end that is insertable through the head and into the aperture. In use, the hook is guided under the vessel to be ligated, and the rod is inserted through the aperture so that the finger grasps the ligature. The rod is then retracted into the head, pulling the ligature with it. The loops of the ligature are then manually slid off the head and over the portion of the ligature pulled toward the head by the rod, and then manually tightened to form a knot around the vessel. This need for the surgeon to reach into the surgical sight with his or her fingers to manipulate and tighten the ligature loops manually thus necessitates an enlarged surgical opening, thereby making a device of this type unsuitable for minimally invasive surgery, such as laparoscopy.

U.S. Pat. No. 5,059,201—Asnis discloses a tool that can be used for ligating a vessel during a laparoscopic procedure. The device includes an elongate outer tube with a bracket on the end. The outer tube carries an axially-movable inner tube, which, in turn, contains an axially-movable shaft with a notch on its end. One end of a suture is clamped to the handle end of the device and is threaded across the bracket. The bracket is placed under a vessel, and the inner tube is extended to capture the vessel. The shaft is then extended through a hole in the bracket to capture the suture in the notch of the shaft. The shaft and the inner tube are then withdrawn into the outer tube to draw the suture around the vessel. A slip knot can then be formed around the vessel, but the knot must be tightened with a separate implement comprising a shaft with a ring at one end. In other words, the Asnis device lacks self-contained means for manipulating and tightening the knot, requiring a separate tool for this task.

U.S. Pat. No. 2,455,833—Trombetta and U.S. Pat. No. 3,985,138—Jarvik disclose ligating devices having clamping jaws for grasping a vessel to be ligated while a suture is tied around the vessel. While these devices (and especially the Jarvik device) may be adapted for use through a trocar, both devices require severing and clamping of the vessel prior to the application of the ligatures, and thus may be disadvantageous where clamping is sought to be avoided or minimized.

Other devices for applying ligatures are disclosed in U.S. Pat. No. 1,400,653—Barbour; U.S. Pat. No. 1,545,682—Nelson; U.S. Pat. No. 3,040,747—Wood; and British Patent No. 479,719—Webb et al. The devices are typically forceps-like implements that are not adapted for insertion and use through a trocar, and that may require clamping of the vessel and/or manual manipulation and tightening of the ligature knot.

Thus, there has been an as-yet unfulfilled need for a ligature tying device that is suitable for use through a trocar for laparoscopic procedures, that includes self-contained means for manipulating and tightening the ligature knot through the trocar without the need for manual manipulation and tightening, and that do not require clamping of the vessel. Furthermore, it would be advantageous to provide such a device that is also simple to manufacture and to use, and that does not require the use of new, complex suture knots. It would be further advantageous to provide a device of this nature that can be made in a disposable or single use embodiment.

SUMMARY OF THE INVENTION

Broadly, the present invention is a suture ligation device, comprising an elongate outer tube having a patient, or distal end and an operator, or proximal end. Extending distally from the patient end of the outer tube are first means for (1) grasping and isolating a vessel or duct, and (2) holding the tag end of a suture. The outer tube carries within it axially movable second means for releasably holding a plurality of loops of the suture. The second means, in turn, carries within it axially movable, spring-biased third means, for capturing the tag end of the suture from the first means, and for drawing the tag end of the suture through loops released by the second means so as to form and tighten a ligating knot around the vessel.

In a preferred embodiment of the invention, the outer tube has an open patient end, and the first means comprises an arcuate finger having a tip that is spaced from and opposed to the open patient end of the outer tube, the tip being configured so as to hold a portion of the length of a suture, near its tag end, in opposition to the open patient end of the outer tube. The second means comprises an inner tube or mandrel that is axially movable within the outer tube, and that has a distal end protruding from the open patient end of the outer tube. Wrapped around the distal end of the inner tube are several loops formed in the standing part of the suture, the tag end of which is held by the finger. The third means comprises a spring-loaded push rod disposed within the inner tube, the distal end of the push rod having a hook that is extensible from the inner tube for grasping the tag end of the suture from the finger. The spring bias of the rod is such as to urge the rod proximally, that is, away from the finger and toward the operator.

To perform a ligation, the patient end of the outer tube is passed down a trocar to the surgical site. The outer tube is manipulated so that the finger isolates the vessel or duct, and captures the vessel or duct in the arcuate bend of the finger, between the tip of the finger and the open patient end of the outer tube. The push rod is moved distally, against the bias of its spring, until the hook at its distal end emerges from the distal or patient end of the inner tube and captures the tag end of the suture from the finger. The push rod is then released, and its spring bias causes it to move proximally, looping the tag end of the suture over the captured vessel or duct, and into the inner tube, thereby passing the tag end of the suture through the loops carried on the distal end of the inner tube.

The inner tube is now pulled proximally through the outer tube, dropping the loops off of its distal end, and onto the tag end of the suture, thereby forming a loose knot. The knot is then tightened on the tag end of the suture as the tag end is pulled through the loops by the continued proximal movement of the push rod, the engagement of the suture against the distal side of the finger providing the required counter-tension. As the tightening tension increases, the finger flexes, thereby releasing the suture, which then forms a loop that tightens around the vessel or duct. Continued pulling of the tag end by the push rod causes the knot to lodge in a notch in the patient end of the outer tube, whereby further proximal movement of the knot is halted. Continued tension applied to the tag end by the push rod brings the vessel or duct up against the knot and constricts the suture around the vessel or duct until ligation is completed. The suture is finally cut above the knot by rotating the device to bring the tag end and the standing part of the suture into contact with a cutting blade built into the distal end of the outer tube. The finger is then disengaged from the vessel or duct, and the ligation device is withdrawn from the trocar.

As will be better appreciated from the detailed description that follows, the present invention offers several advantages over prior art ligation devices. First, it is especially well-suited to laparoscopic surgery, by virtue of its ability to be inserted into a trocar, and by its ability to tighten the ligature knot without the use of either a separate implement or the surgeon's manual manipulation of the suture. Second, the device can be supplied with the suture pre-loaded, and it does not require the surgeon to learn new or complex ligature knots. In addition, a ligature device in accordance with the present invention can be inexpensively manufactured, and thus is adapted for disposable, single-use embodiments. Furthermore, use of the present invention does not require clamping of the vessel or duct prior to ligation. Moreover, facility in using the present invention may be easily acquired, especially as a result of its automatic knot-tightening capability.

These and other advantages of the present invention will be made apparent in the detailed description that follows.

BRIEF DESCRIPTION OF THE DRAWINGS

FIG. 1 is a perspective view of a laparoscopic ligation device in accordance with a preferred embodiment of the present invention;

FIG. 2 is a plan view of the distal portion device, taken along line 2—2 of FIG. 1;

FIG. 3 is a plan view of the proximal portion of the device, taken along line 3—3 of FIG. 1;

FIG. 4 is an axial cross-sectional view, taken along line 4—4 of FIG. 1;

FIG. 5 is an enlarged, detailed, fragmentary view of the portion of the device enclosed within the broken outline 5 in FIG. 4;

FIG. 9 is an axial cross-sectional view of a laparoscopic trocar inserted into a patient's abdomen via a laparoscopy incision;

FIG. 10 is a view similar to that of FIG. 9, but showing the device of FIG. 1, in elevation, disposed within the trocar of FIG. 9;

FIG. 27 is a perspective view of a laparoscopic ligation device in accordance with an alternative embodiment of the invention;

FIG. 28 is a fragmentary top plan view of the proximal portion of the device of FIG. 27, taken along line 28—28 of FIG. 27;

FIG. 29 is an axial cross-sectional view, taken along line 29—29 of FIG. 27; and FIG. 30 is an enlarged, detailed, fragmentary view of the portion of the device enclosed within the broken outline 30 in FIG. 29.

DETAILED DESCRIPTION OF THE INVENTION

Figure 6:
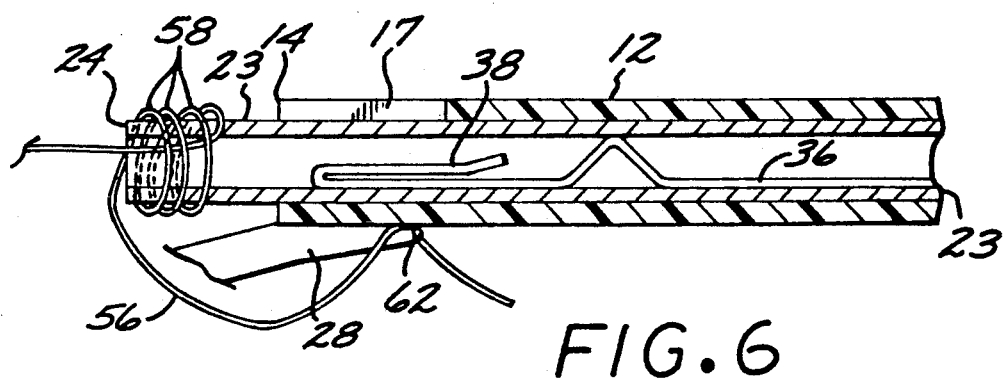
FIG. 6 is a fragmentary, axial, cross-sectional view of the distal portion of the device, showing the suture loops wrapped around the inner tube.

Referring first to FIGS. 1-8 of the drawings, a laparoscopic ligation device 10, in accordance with a preferred embodiment of the invention, is shown. The device 10 comprises an elongate outer tube 12, having a distal or patient end 14 and a proximal or operator portion 16. The distal end 14 of the outer tube 12 is provided with an acutely-angled notch 17, the purpose of which will be described below. The proximal portion 16 of the outer tube 12 is fixed in a tubular sleeve 18 having an enlarged diameter proximal end 19 that abuts against the distal end of a hollow, cylindrical handle member 20. The handle member 20 and the sleeve 18 are detachably joined together by means such as a heat stake 21, as best shown in FIGS. 3 and 5. The interior of the handle 20 defines an axial internal chamber 22.

An elongate inner tube 23 or mandrel is disposed within the outer tube 12 for axial movement therein. The inner tube 23 has a distal or patient end 24 that normally protrudes through, and extends distally from, the open distal end of the outer tube 12. The inner tube 23 extends from its distal end 24, through the proximal portion 16 of the outer tube 12 (which resides in the sleeve 18), to a proximal end 26 that is fixed to the distal end of the handle member 20.

Figure 12:
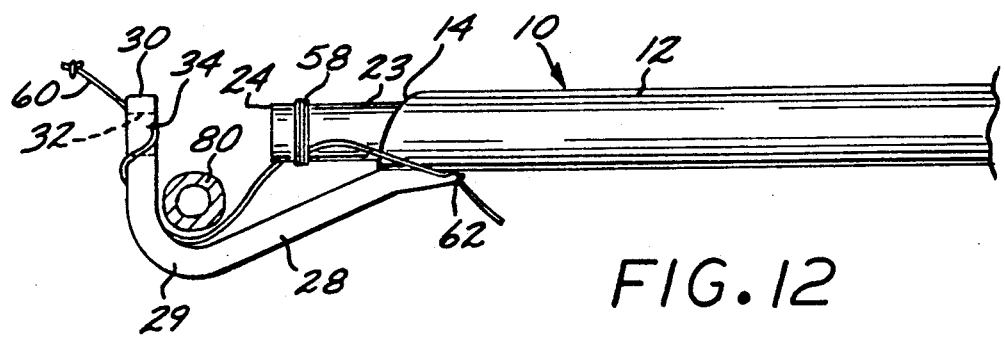
FIG. 12 is an elevational view of the distal portion of the device, showing the step of engaging a vessel to be ligated.
Figure 13:
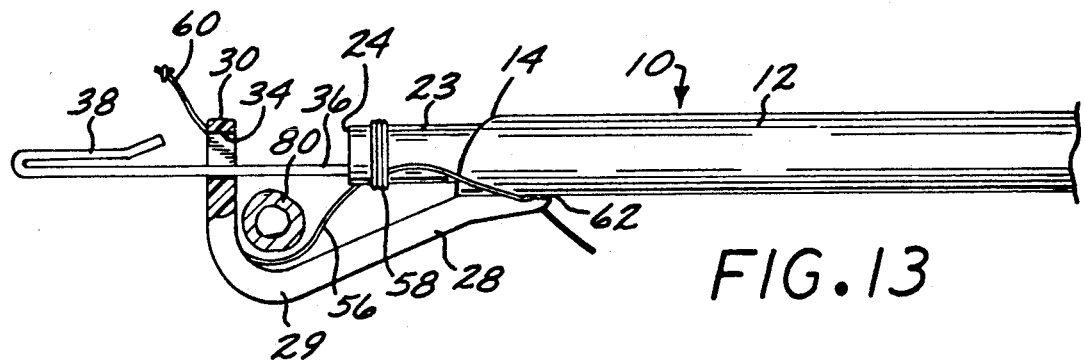
FIG. 13 is an elevational view of the distal portion of the device, showing the step of extending a spring-loaded plunger, disposed within the inner tube of the device, toward and beyond the vessel engaging finger, prior to capturing the tag end of the suture.

Attached to the outer tube 12 near its distal end 14, and extending distally therefrom, is a curved finger 28. The finger 28 has an arcuate bend 29, and a substantially vertical portion that terminates in a tip 30 that is spaced from, and opposed to, the open distal end 14 of the outer tube 12. A suture access aperture 32 is provided near the tip 30 of the finger 28. As best shown in FIGS. 12 and 13, a lateral suture retention groove 34 is formed in the finger tip 30, on either side of the aperture 32, the grooves 34 being located on the proximal side of the finger tip 30, that is, on the side facing the open distal end of the inner tube 23.

An elongate push rod 36 is disposed longitudinally within the inner tube 23 for axial movement therein between first (proximal) and second (distal) axial positions. The push rod 36 has a distal portion provided with suture grasping means, such as a hook 38, and a proximal portion 40 that extends through the axial internal chamber 22 of the handle member 20. A piston or plunger 42 is disposed within the chamber 22, and has a distal end 44 residing within the chamber 22, and a proximal end formed as a manual grip or knob 46 that protrudes from the open proximal end of the chamber 22. The plunger 42 is disposed within the chamber 22 for axial movement therein between first (proximal) and second (distal) axial positions, respectively corresponding to the first and second positions of the push rod 36.

Biasing means, such as a coil spring 48, are disposed within the chamber 22 so as to engage against the distal end 44 of the plunger 42 and a distal interior wall surface 50 of the chamber 22. The spring 48 biases the plunger 42, and therefore also the push rod 36, proximally, that is, toward their respective first positions.

Extending radially from the external surface of the plunger 42 is a pin 52 that rides in a longitudinal slot 54 formed in the adjacent wall surface of the handle member 20. The engagement of the pin 52 in the slot 54 prevents the rotation of the plunger 42 relative to the handle member 20, while the proximal and distal ends of the slot 54 define the proximal and distal limits of travel, respectively, of the plunger 42.

The operation of the ligation device 10 is illustrated in FIGS. 6 through 26.

Figure 7:
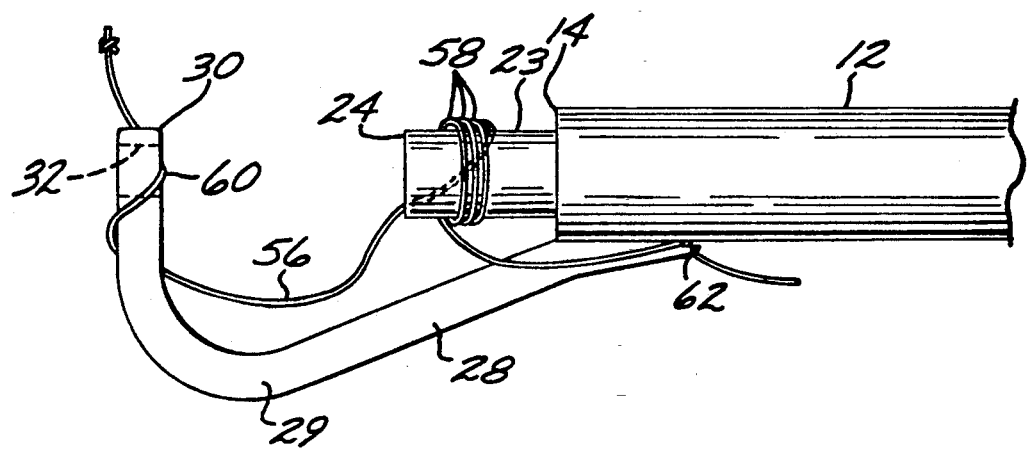
FIG. 7 is a fragmentary elevational view of the distal portion of the device, loaded with a length of suture, prior to performing a ligation.
Figure 8:
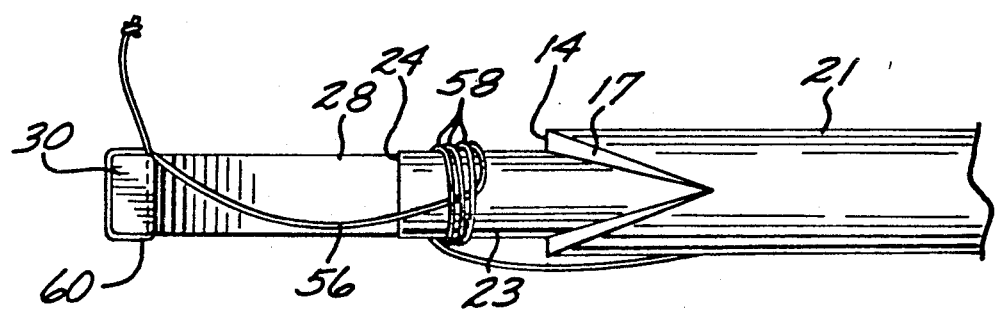
FIG. 8 is a fragmentary top plan view of the distal portion of the device, loaded with a length of suture, prior to performing a ligation.
Figure 11:
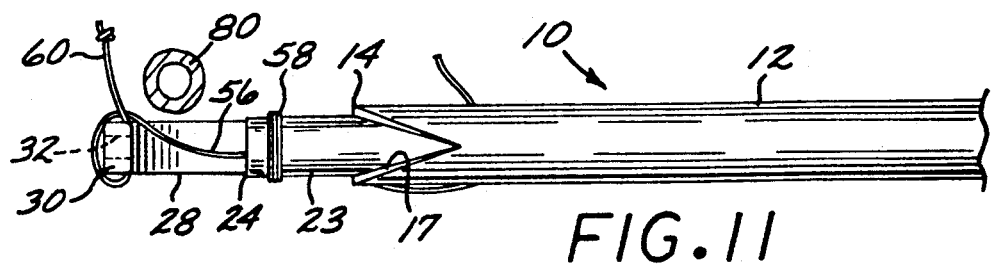
FIG. 11 is a top plan view of the distal portion of the device, prior to engagement with a vessel to be ligated.

Referring first to FIGS. 6, 7, and 8, the ligation device 10 is loaded with a length of suture 56, by wrapping at least one loop 58 (and preferably several loops as shown) of the suture 56 around the distal portion of the inner tube 23, with the inner tube in its first (distal) position, that is, extending distally from the open distal end 14 of the outer tube 12. The loops 58 are formed in the standing part of the suture 56, leaving a free or tag end 60 that is wrapped around the tip 30 of the finger 28, so as to be seated in the lateral grooves 34. (See FIGS. 12 and 13.) So positioned, the tag end 60 extends laterally across the aperture 32 in the finger tip 30. The tag end 60 is advantageously terminated by a simple knot 61 (such as an over-hand knot) to provide a better grasp by the hook 38. The end of the suture 56 opposite the tag end 60 may be held in a notch 62 formed at the juncture between the finger 28 and the outer tube 12.

The ligation device 10, loaded with the suture 56 as described above, is now ready for insertion into a laparoscopic surgical site, as illustrated in FIGS. 9 and 10. The site is typically formed as a small incision, or more accurately, a puncture, through a patient's skin and abdominal wall (indicated generally by the numeral 64 in the drawings), through which a trocar 66 is inserted to provide access to the tissue or organ (not shown) upon which the surgical procedure is performed.

The trocar 66 is a well-known surgical implement, and it is not a part of the subject invention. Briefly described, the trocar 66 comprises a tubular collar 68 having a neck 70 that seals against the skin around the surgical opening. Seated within the neck 70 is one end of a tubular conduit 72, the other end of which opens proximate the tissue or organ upon which the surgical procedure is performed. The outer end of the collar 68 is provided with an annular seat 74 defining a central access orifice 76. The orifice 76 is sealed on its inner side by a hinged cover 78.

As shown in FIG. 10, when a tissue or organ is to be ligated during, or at the conclusion of, the surgical procedure, the ligation device 10, loaded with the suture 56, is inserted into the trocar 66, so that the finger 28 is near the tissue or organ to be ligated. The insertion of the ligation device 10 involves pushing the ligation device against the cover 78 so that the cover 78 pivots on its hinge (not shown), thereby opening the access orifice 76. The outside diameter of the sleeve 18 and the diameter of the orifice 76 are preferably sized so that a seal is formed between the sleeve and the periphery of the orifice 76. As is standard in laparoscopic surgery, visualization of the insertion (and subsequent manipulation) of the ligation device is through a conventional videoscopic implement (not shown), inserted through a separate trocar (not shown), installed in an adjacent laparoscopic puncture site.

The steps in the method of using the ligation device are illustrated in FIGS. 11 through 26. As shown in the figures, the device 10 is used to ligate a blood vessel 80, but the device can be used, in a similar sequence of steps, to ligate a wide variety of tissues and organs.

Figure 14:
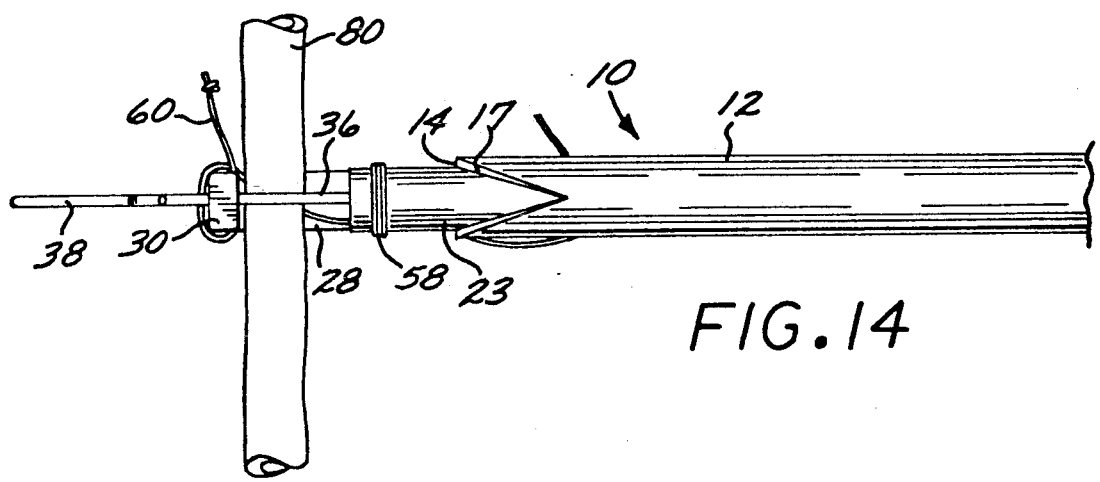
FIG. 14 is a top plan view of the distal portion of the device, showing the same step as shown in FIG. 13.
Figure 15:
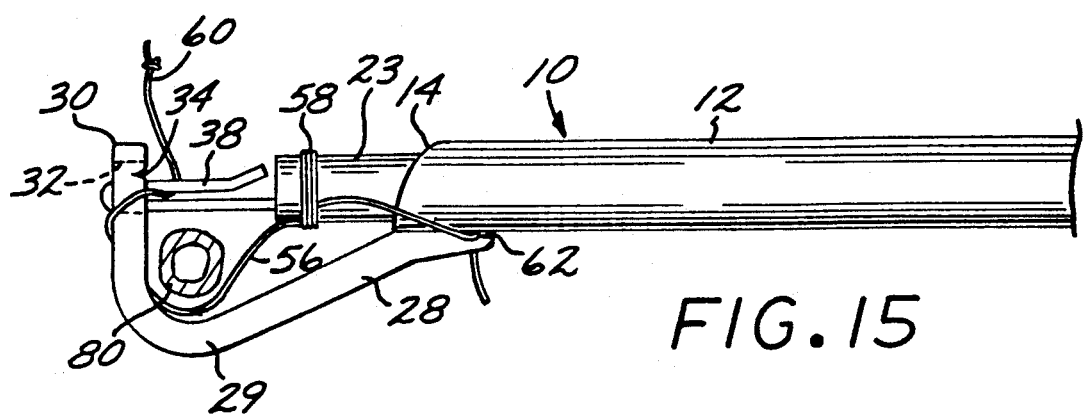
FIG. 15 is an elevational view of the distal portion of the device, showing the step of capturing the tag end of the suture in a hook on the distal end of the plunger.
Figure 16:
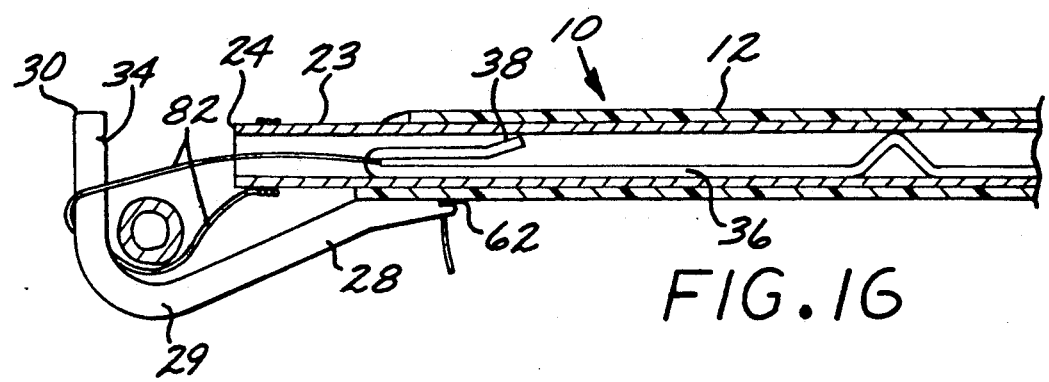
FIG. 16 is a cross-sectional view of the distal portion of the device, showing the step of drawing the tag end of the suture through the suture loops carried on the outside of the inner tube.
Figure 17:
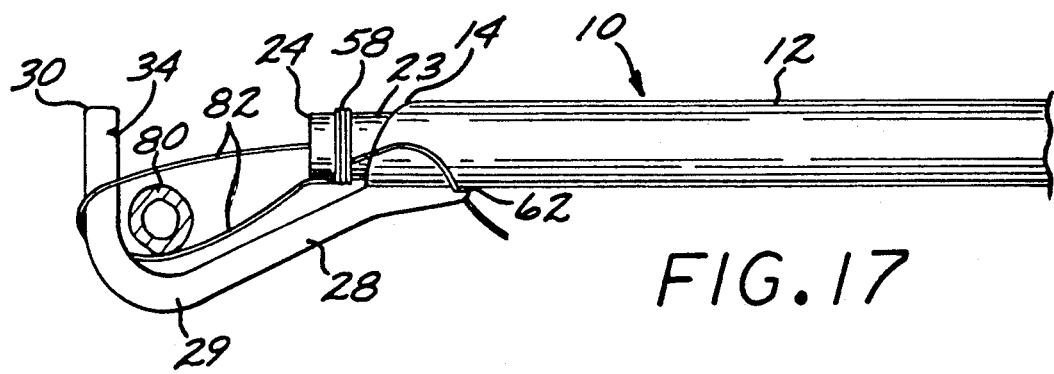
FIG. 17 is an elevational view of the distal end of the device, showing a further progression of the step shown in FIG. 16.

The device is first positioned with the finger 28 adjacent the vessel 80 (FIG. 11), and is then manipulated first to isolate the vessel 80 with the finger tip 30, and then to seat the vessel 80 in the bend 29 of the finger 28 (FIG. 12). As shown in FIGS. 13 and 14, the push rod 36 is then extended from its first or proximal position to its second or distal position, by the surgeon pushing the plunger 42 distally, so that the push rod 36 passes over the vessel 80, with its hook 38 passing through and past the suture access aperture 32 in the finger tip 30. The plunger 42 is then released, allowing the push rod 36 to be pulled back to its first or proximal position by the spring 48. On its return back through the suture access aperture 32, the hook 38 snags the tag end 60 of the suture 56 (FIG. 15), and pulls the tag end 60 out of the retention grooves 34, proximally over the vessel 80, and into the distal or patient end 24 of the inner tube 23 (FIG. 16). The knot 61 helps keep the tag end 60 from slipping out of the hook 38 while being pulled in the proximal direction. The proximal motion of the hook 38 thus creates a suture loop 82 around the vessel 80, while also pulling the tag end 60 of the suture through the suture loops 58 wrapped around the outside of the inner tube 23 (FIG. 17).

Figure 18:
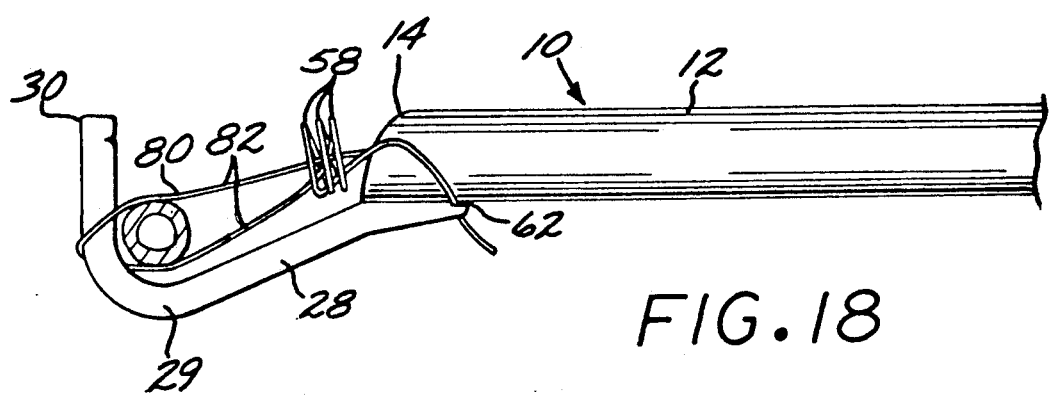
FIG. 18 is an elevational view of the distal end of the device, showing the step of withdrawing the inner tube to drop the suture loops onto the tag end of the suture to form a knot.

The next step, as shown in FIG. 18, is for the inner tube 23 to be drawn proximally into the outer tube 12, thereby causing the suture loops 58 to be dropped over the tag end 60 of the suture 56, thereby forming a loose knot 84. This is done by twisting the handle member 20 with respect to the sleeve 18, thereby breaking the heat stake connection 21 between the two, and then pulling the handle member proximally away from the sleeve 18.

Figure 19:
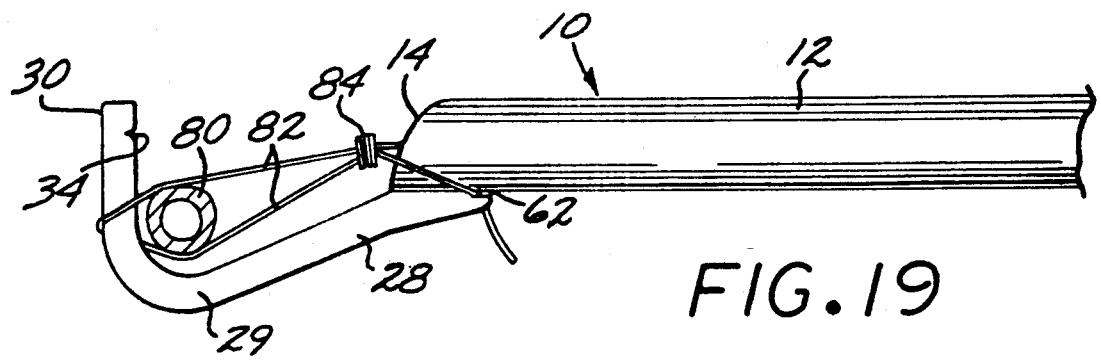
FIGS. 19, 20, and 21 are elevational views of the distal end of the device, showing the progression of the step of tightening the knot onto the tag end of the suture, FIG. 21 further showing the suture being released from the finger to form a loop around the vessel.
Figure 20:
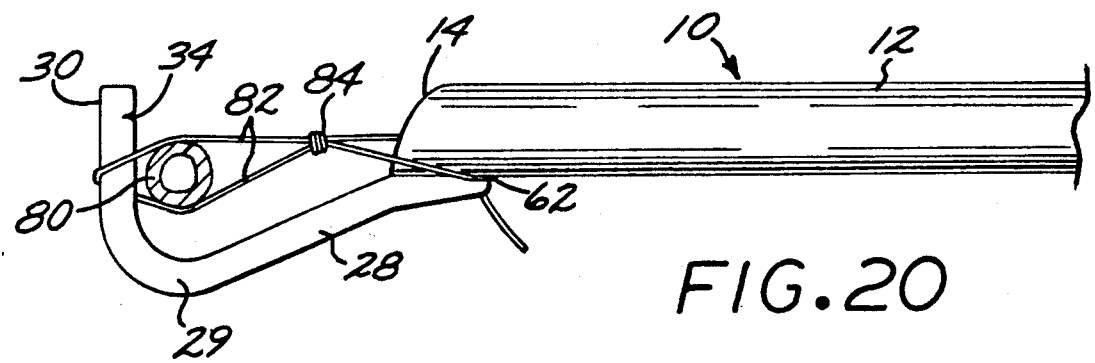
Figure 21:
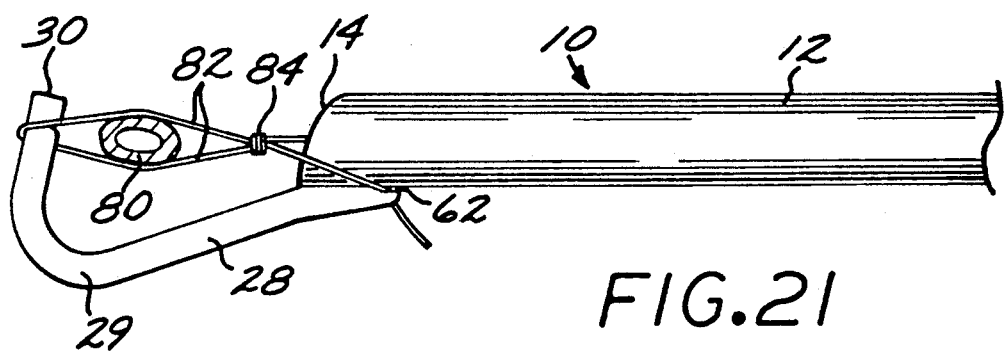
Figure 22:
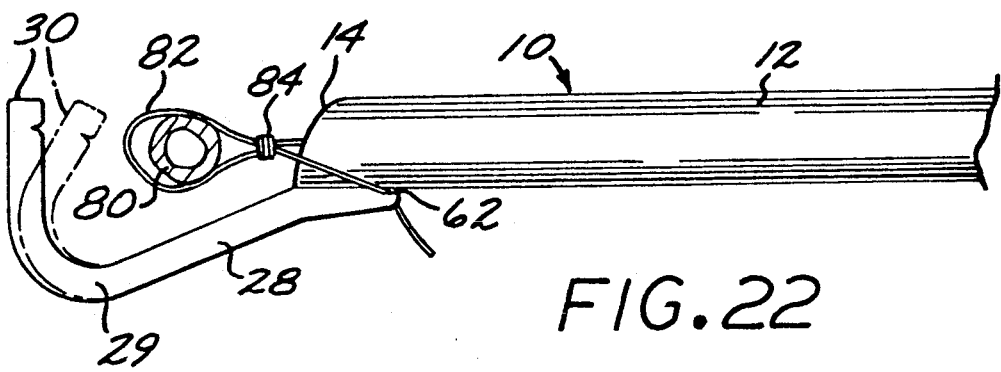
FIG. 22 is an elevational view of the distal portion of the device, showing the tightening of the loop around the vessel, the suture having been released from the finger.

The process of tightening the knot 84, and drawing the knot 84 and the vessel 80 together, is shown in FIGS. 19 through 22. This tightening and drawing process is accomplished by the continued proximal movement of the push rod 36, under the biasing force of the spring 48. Tension for tightening the knot is provided by the engagement of the suture loop 82 with the finger 28. In FIG. 19, the knot 84 is still relatively loose and widely separated from the vessel 80. The suture loop 82 encompasses both the finger 28 and the vessel 80. FIG. 20 shows the knot having been drawn tighter and closer to the vessel 80 by the proximal movement of the push rod 36. Continued tightening of the knot 84, by the further proximal movement of the push rod 36, is shown in FIG. 21, which also shows the finger tip 30 beginning to flex toward the distal end 14 of the outer tube 12, as a result of the tension applied by the proximally-moving push rod 36 to the suture loop 82. The flexing of the finger tip 30 finally results in the suture loop 82 being released, as shown in FIG. 22, allowing the suture loop 82 to begin to close around the vessel 80, as the knot 84 continues to be tightened and drawn closer to the vessel.

Figure 23:
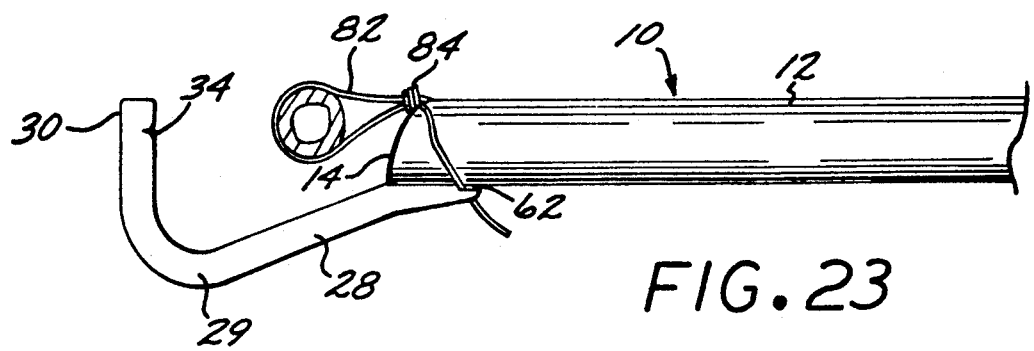
FIG. 23 is an elevational view of the distal portion of the device, showing the knot having reached its proximal limit of travel, having become seated in a notch in the distal end of the outer tube.
Figure 24:
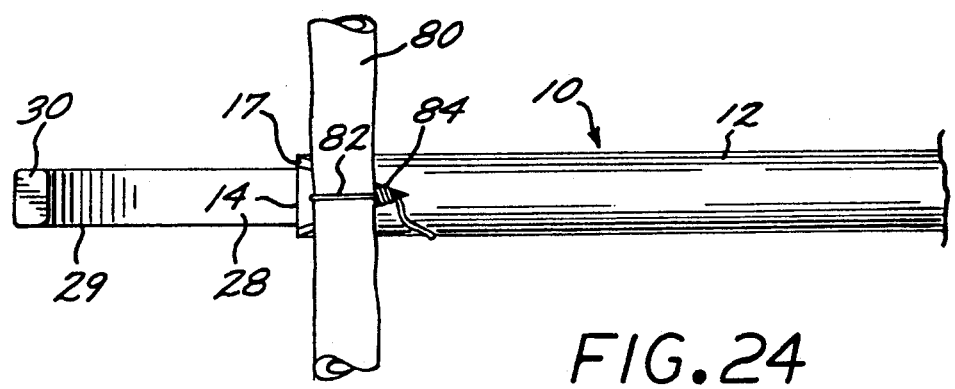
FIGS. 24 and 25 are top plan views of the distal portion of the device, showing the progression of the step of constricting the vessel by tightening the loop around it.
Figure 25:
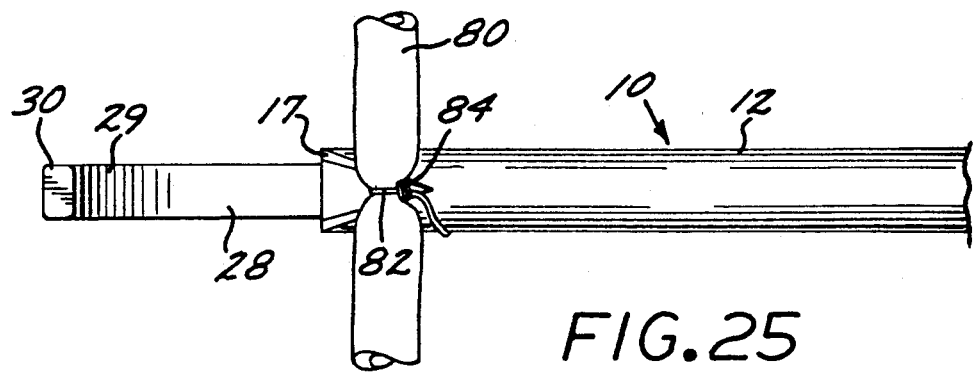

FIGS. 23 and 24 show the knot 84 at its limit of travel in the proximate direction, having been drawn up into the notch 17 at the distal end 14 of the outer tube 12. While the proximal movement of the knot 84 is stopped in the notch 17, the tag end 60 of the suture is still pulled proximally (that is, away from the knot 84) by the continued proximal movement of the push rod 36, thereby further tightening the knot. Moreover, the continued pulling of the tag end 60 through the knot 84 causes the loop 82 to tighten around the vessel 80, until, as shown in FIG. 25, the vessel is completely ligated.

Figure 26:
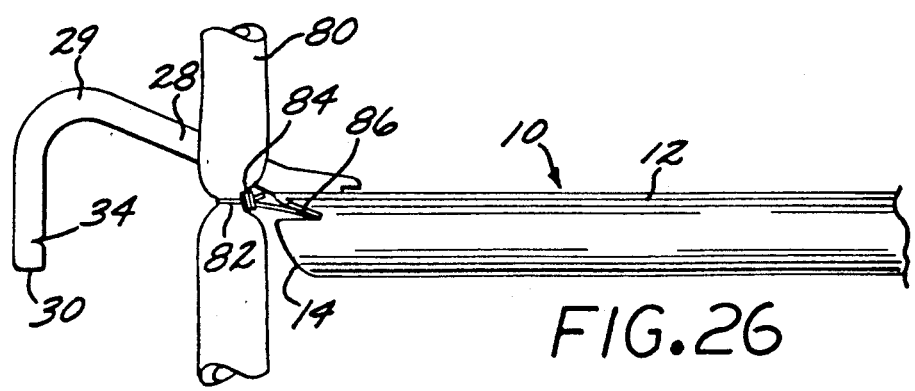
FIG. 26 is a top plan view, similar to that of FIGS. 24 and 25, showing the vessel having been ligated by the complete tightening of the loop around it, and showing the step of cutting the suture to free the ligation device prior to its withdrawal from the trocar.

Finally, the ends of the suture on either side of the knot 84 are cut off, so that the ligation device 10 can be removed from the completely ligated vessel 80. This can be accomplished by passing a cutting tool (such as a scalpel or scissors) down into the trocar. Preferably, however, this is accomplished, as shown in FIG. 26, by providing a cutting blade 86 in the distal end 14 of the outer tube 12, near the juncture between the outer tube 12 and the hook 28. The cutting blade is employed by manipulating the ligation device so as to free the suture 56 from the notch 62 at the juncture between the finger 28 and the outer tube 12, and so as to free the knot 84 from the notch 17 at the distal end 14 of the outer tube 12. The device is then axially rotated to bring the cutting blade 86 to bear against the tag end 60 and the opposite end of the suture 56, thereby to sever these ends from the knot.

FIGS. 27 through 30 illustrate another ligation device 110, in accordance with an alternative embodiment of the invention. The ligation device 110 includes an elongate outer tube 112 having a distal end 114, a central, main portion 116, and a proximal portion 118. The distal end 114 of the outer tube 112 is provided with an acutely-angled, knot-tightening notch 120. The proximal portion 118 is detachably joined to the main portion 116 by means such as a heat stake 122.

An elongate inner tube or mandrel 124 is disposed within the outer tube 112 for axial movement therein. The inner tube 124 has a distal end 126 that normally protrudes through, and extends distally from, the open distal end 114 of the outer tube 112. The inner tube 124 extends from its distal end 126, through the main portion 116 of the outer tube 112, to a proximal end 128 that is fixed within the proximal portion 118 of the outer tube 112.

Attached to the outer tube 112 near its distal end 114, and extending distally therefrom, is a finger 130, having an arcuate bend 131, and a substantially vertical portion 132 terminating in a tip 133 that is spaced from the open distal end 114 of the outer tube 112. The finger tip 133 is slightly offset from axial alignment with the outer tube 112, for reasons to be made clear below. A lateral suture retention groove 134 is formed in the finger tip 133, on the side facing the distal ends of the inner and outer tubes. A vertically-oriented, suture-holding clip 136 is attached to the distal side of the substantially vertical finger portion 132, that is, on the side opposite the groove 134. The suture-holding clip 136 is located so as to hold a length of suture 138 against the distal side of the finger portion 132, with the tag end of the suture 138 seated in the groove 134. A suture-holding notch 139 is formed at the juncture between the finger 130 and the outer tube 112.

An elongate posh rod 140 is disposed longitudinally within the inner tube 124 for axial movement therein between a first, proximal position, and a second, distal position. The push rod 140 has a distal end provided with suture grasping means, such as a hook 142, and a proximal portion that extends proximally out of the proximal portion 118 of the outer tube 112, terminating in a button 144. Biasing means, such as a coiled wire spring 146, are connected between the button 144 and the proximal portion 118 of the outer tube 112, biasing the push rod 140 toward its first, proximal position.

Disposed on the push rod 140 proximally of the hook 142 is a first protuberance forming a first stop element 148. A second protuberance, forming a second stop element 150, is disposed on the interior surface of the inner tube 124. The first stop element 148 abuts against the second stop element 150 to limit the travel of the push rod 140 in the proximal direction under the force of the spring 146, thereby defining the first position of the push rod.

The method of using the alternative embodiment ligation device 110 is very similar to the method of using the preferred embodiment device 10. The device 110 is loaded with a length of suture 138 by wrapping several turns of the standing part of the suture around the distal end of the inner tube 124. The suture is then passed around the distal side of the vertical finger portion 132, held in place by the clip 136, the tag end of the suture being seated in the groove 134 in the finger tip 133. The opposite end of the suture 138 is held in the notch 139 at the juncture between the finger 130 and the outer tube 112.

The device 110 is then directed to the tissue or organ to be ligated through a trocar, as described above. The tissue or organ (e.g., a blood vessel) is isolated by the finger tip 133 and seated in the finger bend 131, as previously described. The push rod is pushed distally, to its second position, by manual pressure applied to the button 144, until its hook 142 extends past the finger tip 133, the tip being axially offset, as mentioned above. When the pressure on the button is relieved, the push rod begins its return, under the force of the spring 146, to its first, proximal position, and the tag end of the suture is captured by the hook 142 as it passes by the finger tip 133 on its return travel.

The tag end of the suture is carried into the inner tube 124, as with the previously-described embodiment, and the turns of the suture are dropped onto the tag end by the surgeon manually pulling the inner tube proximally with respect to the outer tube by first radially twisting the outer tube proximal portion 118 with respect to the main portion 116 to break the heat stake 120, and then by pulling the proximal portion 118 proximally away from the main portion. Since the inner tube 124 is fixed to the proximal portion 118 of the outer tube, the movement of the outer tube proximal portion 118 away from the outer tube main portion 116 causes the inner tube 124 to be withdrawn into the outer tube 112, thereby dropping the suture turns onto the tag end of the suture to form a loose knot, as previously described.

As with the previously-described embodiment, the knot and the vessel are drawn together, and the knot is tightened, by the movement of the hook 142 toward its proximal (first) position, carrying the tag end of the suture with it. The tension applied by the hook 142 to the suture causes the suture to be released from the clip 136 on the finger 130, thereby forming a loop around the vessel, which loop is tightened by the movement of the hook 142. Finally, the knot is drawn up into the notch 120 for final tightening, the ligation of the vessel being then completed, as described above. With this alternative embodiment, it is contemplated that the final step of cutting off the knot would be accomplished by a separate implement, although a cutting blade (not shown) can be provided in the outer tube, as in the previously-described embodiment.

From the foregoing description, it can be seen that the present invention offers several distinct advantages over prior art devices of this general nature. First, it is easily appreciated that the invention is especially well-adapted for laparoscopic surgery performed through a trocar. Second, the invention allows the surgeon to (1) engage and isolate the tissue or organ to be ligated, (2) wrap the suture around the tissue or organ, (3) form a ligating knot, (4) tighten the ligature and the knot so as to ligate the tissue or organ, and (5) cut the knot off of the suture, all with a single implement. Furthermore, all of these steps are performed without the need for any manual manipulation of the suture; nor is there any need to clamp the tissue or organ. Moreover, since the device forms, ties, and tightens the knot automatically, there is no need for the surgeon to learn any new or complex knots. Consequently, facility in using the present invention is easily acquired. Furthermore, the invention can be inexpensively manufactured, lending itself to disposable, single use embodiments, such as those described above.

While two specific embodiments of the invention have been described above, it will be appreciated that a number of variations and modifications will suggest themselves to those skilled in the pertinent arts. For example, if a reusable device is desired, the heat stake juncture between the handle member 20 and the sleeve 18 in the first embodiment described above can be replaced with a pin and socket assembly, or a threaded fitting between the two members. It may also be desirable to provide different sizes and configurations for the tissue-engaging finger, depending upon the type of tissue or organ to be ligated. To this end, it may be desirable to have a finger that is removably attached to the outer tube, so that the finger can be replaced. In addition, the specific means employed to hold the suture onto the finger may be varied to suit different application or the individual preferences of the surgeon. For example, The offset finger and clip used in the second embodiment described above can be used in the first embodiment, while the apertured finger tip used in the first embodiment can be employed in the second. Still other types of suture holding means may be employed without departing from the scope of the invention. Likewise, a wide variety of means can be employed for biasing the push rod toward its proximal position. These modifications and variations, and others that may suggest themselves, are considered to be within the spirit and scope of the present invention, as defined in the claims that follow.

What is claimed is:

1. A ligation device for tying a suture around a selected bodily vessel or duct, in combination with a suture having a tag end and a standing part with a loop formed therein, the device comprising:
   an elongate hollow tube extending axially between a proximal portion and a distal end;
   first means, attached to the elongate hollow tube near its distal end, for isolating and engaging a selected vessel or duct, and for releasably holding the tag end of the suture;
   second means, disposed within the elongate hollow tube for axial movement therein between a first axial position and a second axial position, for holding the loop formed in the standing part of the suture when in the first axial position and releasing the loop when in the second axial position;
   first actuation means for selectively moving the second means from the first position to the second position;
   third means, disposed within the second means for axial movement therein between a first axial position and a second axial position, for grasping the tag end of the suture directly from the first means when in the second axial position and when the tag end is held by the first means, and for pulling the tag end around the selected vessel or duct and toward the proximal portion of the tube as the third means moves to its first axial position; and
   second actuation means for selectively moving the third means between its first and second axial positions;
   whereby the movement of the third means from its second position to its first position carries the tag end of the suture into the second means and within the loop held on the second means, and whereby the movement of the second means from its first position to its second position releases the loop onto the tag end of the suture to form a knot in the suture that is tightened around the vessel or duct by the further movement of the third means toward its first position.

2. The device of claim 1, wherein the second actuation means includes biasing means for biasing the third means toward its first axial position.

3. The device of claim 1, wherein the second means comprises an elongate member having a distal end near which the suture loop is held, and a proximal end, and wherein the first actuation means comprises a manually-actuable element that is fixed to the proximal end of the elongate member and detachably joined to the proximal portion of the elongate, hollow tube.

4. The device of claim 3, wherein the elongate hollow tube is a first elongate hollow tube, and wherein the elongate member comprises a second elongate hollow tube.

5. The device of claim 4, wherein the third means comprises a push rod disposed longitudinally within the second tube and having a distal end and a proximal end, the distal end including grasping means for grasping the tag end of the suture from the first means, the proximal end being operatively engaged by the second actuation means.

6. The device of claim 5, wherein the manually-actuable element comprises a hollow cylinder having an axial internal chamber, and wherein the second actuation means comprises:
   a piston disposed within the axial internal chamber for movement therein between first and second axial positions respectively corresponding to the first and second axial positions of the third means, the piston being connected to the proximal end of the push rod; and
   a spring disposed within the axial internal chamber so as to bias the piston toward its first axial position.

7. The device of claim 5, wherein the the second actuation means comprises:
   a knob attached to the proximal end of the push rod; and
   biasing means, connected between the knob and the manually-actuable element, for biasing the push rod toward the first axial position of the third means.

8. The device of claim 1, wherein the third means comprises a push rod having a distal end and a proximal end, the distal end including grasping means for grasping the tag end of the suture from the first means, the proximal end being operatively engaged by the second actuation means.

9. The device of claim 1, wherein the first means comprises:
   a finger extending between a portion attached to the elongate, hollow tube, and a tip spaced from the distal end of the elongate, hollow tube; and
   suture-holding means on the finger near the tip thereof, for releasably holding the tag end of the suture in a position for being grasped by the third means.

10. The device of claim 9, wherein the suture-holding means comprises:
    an aperture in the finger near its tip; and
    a lateral groove in the finger on either side of the aperture, the grooves being located on the side of the finger facing the distal end of the elongate, hollow tube, the grooves being located and oriented so as to carry the tag end of the suture across the aperture.

11. The device of claim 9, wherein the suture-holding means includes a clip on the finger near its tip.

12. The device of claim 1, further comprising:
    fourth means, adjacent the distal end of the elongate hollow tube, for cutting the knot away from the tag end and standing part of the suture.

13. The device of claim 12, wherein the fourth means comprises a cutting blade disposed in the distal end of the elongate, hollow tube.

14. A ligation device for tying a suture around a selected bodily vessel or duct, in combination with a suture having a tag end and a standing part with a first loop formed therein, the device comprising:
    first means for isolating and engaging a selected vessel or duct, and for releasably holding the tag end of the suture;
    second means, axially movable with respect to the first means between an extended and a withdrawn position, for holding the first loop formed in the standing part of the suture when in the extended position and releasing the first loop when in the withdrawn position;
    first actuation means, operatively connecting the first means and the second means, for selectively moving the second means from the extended position to the withdrawn position;
    third means, disposed within the second means and axially movable with respect to the second means between a withdrawn and an extended position, for grasping the tag end of the suture directly from the first means when in the extended position and when the tag end is held by the first means, and for pulling the tag end around the selected vessel or duct to form a second loop around the selected vessel or duct; and second actuation means for selectively moving the third means between its withdrawn and extended positions;

whereby the movement of the third means from its extended position to its withdrawn position carries the tag end of the suture through the first loop, whereby the movement of the second means from its extended position to its withdrawn position releases the first loop onto the tag end of the suture to form a knot in the suture, and whereby the second loop is constricted around the selected vessel or duct as the knot is tightened by the further movement of the third means from its extended position to its withdrawn position.

15. The device of claim 14, further comprising:
fourth means, operatively connected to the third means, for biasing the third means toward its withdrawn position.

16. The device of claim 15, wherein the first means includes fifth means for cutting the knot away from the tag end and the standing part of the suture.

17. The device of claim 14, wherein the first means comprises:
an elongate, hollow tube having a distal end and a proximal portion;
a finger having a first portion attached to the elongate, hollow tube near its distal end, a second portion forming an arcuate bend, and a tip spaced from the distal end of the elongate, hollow tube; and
suture-holding means near the tip for releasably holding the tag end of the suture in a position for being grasped by the third means.

18. The device of claim 17, wherein the suture-holding means comprises:
an aperture in the finger near its tip; and
a lateral groove in the finger on either side of the aperture, the grooves being located on the side of the finger facing the distal end of the elongate, hollow tube, the grooves being located and oriented so as to carry the tag end of the suture across the aperture.

19. The device of claim 17, wherein the suture-holding means includes a clip on the finger near its tip.

20. The device of claim 14, wherein the third means comprises:
an elongate member having a distal end and a proximal end; and
grasping means, adjacent the distal end, for grasping the tag end of the suture from the first means.

21. The device of claim 20, wherein the second actuation means includes biasing means, operative on the proximal end of the elongate member, for biasing the elongate member toward the withdrawn position of the third means.

22. The device of claim 14, wherein the first means comprises a first elongate, hollow tube having a distal end and a proximal portion, and wherein the second means comprises a second elongate, hollow tube disposed axially within the first elongate, hollow tube, the second elongate, hollow tube having a distal end near which the first loop is held, and a proximal end.

23. The device of claim 22, wherein the first actuation means comprises a manually-actuable element that is fixed to the proximal end of the second elongate, hollow tube and detachably joined to the proximal portion of the first elongate, hollow tube.

24. The device of claim 23, wherein the third means comprises:
an elongate member disposed axially within the second elongate, hollow tube and having a distal end and a proximal end; and
grasping means, adjacent the distal end of the elongate member, for grasping the tag end of the suture from the first means.

25. The device of claim 24, wherein the manually-actuable element comprises a hollow cylinder having an axial internal chamber, and wherein the second actuation means comprises:
a piston disposed within the chamber for movement between first and second axial positions respectively corresponding to the withdrawn and extended positions of the third means, the piston being operatively connected to the proximal end of the elongate member; and
a spring disposed within the chamber so as to bias the piston toward its first axial position.

26. The device of claim 24, wherein the second actuation means comprises:
a knob attached to the proximal end of the elongate member; and
biasing means, connected between the knob and the manually-actuable element, for biasing the elongate member toward the withdrawn position of the third means.

27. A laparoscopic ligation device for tying a suture around a selected bodily vessel or duct, the suture having a standing part and a tag end, the device comprising:
an elongate, hollow, tubular member having a distal end and a proximal portion;
an arcuate finger attached to the elongate, hollow, tubular member near its distal end, and having a tip spaced distally from the distal end of the elongate, hollow, tubular member;
means adjacent the tip of the finger for releasably holding the tag end of the suture;
an elongate, hollow mandrel axially disposed within the tubular member, the mandrel having a proximal end and an open distal end configured for carrying a plurality of loops formed in the standing part of the suture;
first actuation means for selectively moving the mandrel between a first position in which the distal end of the mandrel extends distally from the distal end of the elongate, hollow, tubular member, and a second position in which the distal end of the mandrel is withdrawn into the elongate, hollow, tubular member;
suture-grasping means, axially disposed within the mandrel for movement between a first axial position and a second axial position, for removing the tag end of the suture from the tip of the finger when in the second position, and for pulling the tag end of the suture around the selected vessel or duct and toward the proximal end of the mandrel as the suture-grasping means moves to its first position;
second actuation means for selectively moving the suture-grasping means between its first and second positions; and
biasing means, operative on the second actuation means, for biasing the suture-grasping means toward its first position;

whereby the movement of the suture-grasping means from its second position to its first position carries the tag end of the suture into the open distal end of the mandrel and through the suture loops carried on the mandrel, and whereby the movement of the mandrel from its first position to its second position releases the loops onto the tag end of the suture to form a knot in the suture that is tightened around the vessel or duct by the further movement of the suture-grasping means toward its first position.

28. The device of claim 27, wherein the first actuation means comprises a manually-actuable element that is fixed to the proximal end of the mandrel, and that is detachably joined to the proximal portion of the elongate, hollow tubular member.

29. The device of claim 28, wherein the suture-grasping means comprises:
   a push rod having distal end and a proximal end, the proximal end being operatively engaged by the second actuation means; and
   a grasping member disposed on the distal end of the push rod.

30. The device of claim 29, wherein the manually-actuable element comprises a hollow cylinder having an axial internal chamber, and wherein the second actuation means comprises:
   a piston disposed within the axial internal chamber for movement therein between first and second axial positions respectively corresponding to the first and second axial positions of the suture-grasping means, the piston being connected to the proximal end of the push rod.

31. The device of claim 30, wherein the biasing means comprises:
   a spring disposed within the axial internal chamber so as to bias the piston toward its first axial position.

32. The device of claim 29, wherein the the second actuation means comprises:
   a knob attached to the proximal end of the push rod; wherein the biasing means includes a spring connected between the knob and the manually-actuable element.

33. The device of claim 28, wherein the manually-actuable element is detachably joined to the elongate, hollow tubular member by a frangible heat stake.

34. The device of claim 27, wherein the means for releasably holding the tag end of the suture comprises:
   an aperture in the finger near its tip; and
   a lateral groove in the finger on either side of the aperture, the grooves being located on the side of the finger facing the distal end of the elongate, hollow, tubular member, the grooves being located and oriented so as to carry the tag end of the suture across the aperture.

35. The device of claim 27, wherein the means for releasably holding the tag end of the suture includes a clip on the finger near its tip.

36. The device of claim 27, further comprising:
   suture-cutting means, disposed in the distal end of the elongate hollow tubular member, for cutting the knot away from the tag end and standing part of the suture.

37. A laparoscopic ligation device for tying a suture around a selected bodily vessel or duct through a single surgical passage into a patient's body, in combination with a suture having a tag end and a standing part, the device comprising:

first means, insertable into the passage to the vicinity of the vessel or duct, for (a) isolating and engaging the selected vessel or duct, and (b) releasably holding the tag end of the suture;

second means, disposed within the first means and insertable into the passage together with the first means, for selectively grasping the tag end directly from the first means while the tag end is held by the first means, and for knotting the tag end with the standing part to form a ligature loop around the vessel or duct; and third means, operatively connected to the second means and remote from the first means so as to be located outside the body when the first and second means are inserted into the passage, for actuating the second means to remove the tag end from the first means and to knot the tag end with the standing part.

38. A method of ligating a bodily vessel or duct, comprising the steps of:
   (1) providing an elongate, hollow mandrel having an open distal end and a proximal end, and providing engagement means spaced distally from the distal end for isolating and engaging a vessel or duct;
   (2) providing a length of suture having a standing part and a tag end;
   (3) forming a plurality of loops in the standing part of the length of suture around the distal end of the mandrel, and removably securing the tag end of the suture to the engagement means;
   (4) isolating and engaging the vessel or duct with the engagement means;
   (5) removing the tag end of the suture from the engagement means and drawing it around the vessel or duct, toward the distal end of the mandrel, thereby forming a ligature loop around the vessel or duct;
   (6) drawing the tag end of the suture into the open distal end of the mandrel, thereby passing the tag end through the loops formed on the mandrel;
   (7) dropping the mandrel-formed loops over the tag end of the suture to form a loose knot; and
   (8) drawing the tag end of the suture toward the proximal end of the mandrel to tighten the knot, while thereby closing the ligature loop around the vessel or duct until the vessel or duct is completely ligated.

39. The method of claim 38, further comprising the step of:
   (9) cutting the tightened knot away from the standing part and the tag end of the suture.

40. The method of claim 38, wherein the mandrel is axially disposed within an elongate hollow tube for axial movement therein between an extended position and a withdrawn position, the elongate hollow tube having a distal end near which the engagement means are attached, wherein the step of forming the plurality of loops is performed while the mandrel is in the extended position, and wherein the step of dropping the loops is performed by moving the mandrel to its withdrawn position.

41. The method of claim 38, wherein an elongate member is axially disposed within the mandrel for axial movement therein between an extended position and a withdrawn position, the elongate member having a distal end with a suture-grasping element thereon, wherein the step of removing the tag end of the suture is performed by moving the elongate member to its extended position, so that the tag end is grasped by the grasping element, and wherein the steps of drawing the tag end around the vessel or duct, toward the distal end of the mandrel, into the distal end of the mandrel, and toward the proximal end of the mandrel are performed by moving the elongate member toward the distal end of the mandrel with the tag end grasped by the grasping element.

* * * * *